(12) United States Patent
Friedrichs (10) Patent No.: US 10,973,565 B2
(45) Date of Patent: *Apr. 13, 2021

(54) INTERDIGITATION OF WAVEFORMS FOR DUAL-OUTPUT ELECTROSURGICAL GENERATORS

(71) Applicant: COVIDIEN LP, Mansfield, MA (US)

(72) Inventor: Daniel A. Friedrichs, Aurora, CO (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/508,461

(22) Filed: Jul. 11, 2019

(65) Prior Publication Data
US 2019/0336197 A1 Nov. 7, 2019

Related U.S. Application Data

(63) Continuation of application No. 15/046,115, filed on Feb. 17, 2016, now Pat. No. 10,363,084.
(Continued)

(51) Int. Cl.
*A61B 18/12* (2006.01)
*A61B 18/00* (2006.01)

(52) U.S. Cl.
CPC .. *A61B 18/1206* (2013.01); *A61B 2018/0072* (2013.01); *A61B 2018/0075* (2013.01); *A61B 2018/00702* (2013.01); *A61B 2018/00732* (2013.01); *A61B 2018/00767* (2013.01); *A61B 2018/00773* (2013.01); *A61B 2018/128* (2013.01); *A61B 2018/1266* (2013.01)

(58) Field of Classification Search
CPC .. A61B 2018/00702; A61B 2018/0072; A61B 2018/00732; A61B 2018/0075; A61B 2018/00767; A61B 2018/00773; A61B 2018/1266; A61B 2018/128; A61B 18/1206; A61B 18/1233; A61B 18/1402
See application file for complete search history.

(56) References Cited

U.S. PATENT DOCUMENTS 4,051,855 A * 10/1977 Schneiderman ....... A61B 18/12
 606/42
4,559,943 A 12/1985 Bowers
(Continued)

FOREIGN PATENT DOCUMENTS

EP 2353533 A2 8/2011

OTHER PUBLICATIONS

European Search Report corresponding to European Patent Application No. 16163117.1, completed Jul. 21, 2016 and dated Jul. 28, 2016 (12 pp).
(Continued)

*Primary Examiner* — Thomas A Giuliani
*Assistant Examiner* — Christine A Dedoulis
(74) *Attorney, Agent, or Firm* — Carter, DeLuca & Farrell LLP (57) ABSTRACT

Disclosed are systems, devices, and methods for interdigitation of waveforms for dual-output electrosurgical generators. Such methods may comprise outputting DC energy from a power supply, converting DC energy from the power supply, by a plurality of amplifiers coupled to the power supply, into a plurality of RF waveforms, and controlling the plurality of RF amplifiers to interdigitate the first and second RF waveforms.

13 Claims, 5 Drawing Sheets

Related U.S. Application Data

(60) Provisional application No. 62/141,594, filed on Apr. 1, 2015.

(56) References Cited

U.S. PATENT DOCUMENTS

| | | |
|---|---|---|
| 5,931,835 A | 8/1999 | Mackey |
| 5,954,686 A * | 9/1999 | Garito .................... A61B 18/12 604/37 |
| 7,094,231 B1 * | 8/2006 | Ellman .............. A61B 18/1206 606/34 |
| 8,298,226 B2 | 10/2012 | Hosier |
| 8,974,449 B2 | 3/2015 | Brannan |
| 9,028,479 B2 | 5/2015 | Orszulak |
| 9,339,324 B2 | 5/2016 | Eisele et al. |
| 2004/0097912 A1 | 5/2004 | Gonnering |
| 2009/0318915 A1 * | 12/2009 | Hosier ................... A61B 18/12 606/33 |

OTHER PUBLICATIONS

European Examination Report, dated Aug. 31, 2017, correposnding to European Application No. 16 163 117.1; 5 pages.

* cited by examiner

INTERDIGITATION OF WAVEFORMS FOR DUAL-OUTPUT ELECTROSURGICAL GENERATORS

CROSS REFERENCE TO RELATED APPLICATION

The present application is a continuation of U.S. patent application Ser. No. 15/046,115, filed Feb. 17, 2016, which claims the benefit of and priority to U.S. Provisional Application Ser. No. 62/141,594, filed on Apr. 1, 2015. The entire contents of each of the foregoing applications are incorporated by reference herein.

BACKGROUND

Technical Field

The present disclosure relates to an electrosurgical system and method for operating an electrosurgical generator. More particularly, the present disclosure relates to a system, method and apparatus for interdigitation of electrosurgical waveforms generated by radiofrequency resonant inverters.

Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue and a return electrode conducts the current back to the generator. A patient return electrode is placed remotely from the active electrode to conduct the current to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

Electrosurgical generators may have multiple outputs to power multiple electrosurgical instruments. When multiple instruments connected to a multiple output electrosurgical generator are activated, the generator delivers the programmed power to the parallel combination of connected instruments. However, prior art generators were not capable of equally distributing power to multiple instruments. Since it was unlikely that multiple instruments would be activated at the exact same time and used on the exact same impedances of tissue, it was not possible to obtain consistent performance with multiple instruments connected to multiple outputs of the electrosurgical generator. Thus, simultaneous activation of multiple instruments using existing generators resulted in poor performance, and in situations where multiple surgeons were operating on a patient simultaneously the results were unpredictable. As a result multiple electrosurgical generators were utilized to provide acceptable performance. Accordingly, there is a need for an electrosurgical generator configured to power multiple electrosurgical instruments that are usable simultaneously and to regulate individually the specified output power for each of the instruments coupled to the generator.

SUMMARY

The present disclosure describes interdigitating waveforms corresponding to power output generated by a dual-output electrosurgical generator. Provided in accordance with the disclosure are devices, systems, and methods for interdigitating such waveforms.

In an aspect of the present disclosure, an electrosurgical generator comprises a power supply configured to output DC energy, a plurality of RF amplifiers coupled to the power supply, each of the plurality of RF amplifiers being configured to convert DC energy from the power supply into an RF waveform, thereby generating a plurality of RF waveforms, and a controller coupled to the power supply and the plurality of RF amplifiers and configured to control the plurality of RF amplifiers to interdigitate the RF waveforms generated by the plurality of RF amplifiers.

In a further aspect of the present disclosure, the electrosurgical generator comprises a plurality of sensors coupled to the plurality of RF amplifiers, each of the plurality of sensors configured to measure at least one property of a corresponding RF waveform of the plurality of RF waveforms supplied by a corresponding RF amplifier of the plurality of RF amplifiers.

In yet a further aspect of the present disclosure, the controller is further coupled to the plurality of sensors and is further configured to control the plurality of RF amplifiers based on the at least one property of the corresponding RF waveform.

In another aspect of the present disclosure, the plurality of RF waveforms are square waveforms.

In yet another aspect of the present disclosure, the controller is further configured to adjust the DC energy supplied by the power supply to the plurality of RF amplifiers based on at least one property of at least one RF waveform of the plurality of RF waveforms.

In another aspect of the present disclosure, at least one of the plurality of RF amplifiers is a non-resonant RF amplifier.

In an aspect of the present disclosure, a system for interdigitating waveforms for a dual-output electrosurgical generator comprises the dual-output electrosurgical generator which comprises a power supply configured to output DC energy, a plurality of RF amplifiers coupled to the power supply, each of the plurality of RF amplifiers being configured to convert DC energy from the power supply into an RF waveform, thereby generating a plurality of RF waveforms, and a controller coupled to the power supply and the plurality of RF amplifiers and configured to control the plurality of RF amplifiers to interdigitate the RF waveforms generated by the plurality of RF amplifiers, and at least two electrosurgical instruments operatively coupled to the dual-output electrosurgical generator, wherein each of the electrosurgical instruments is coupled to one of the plurality of RF amplifiers.

In another aspect of the present disclosure, the electrosurgical generator further comprises a plurality of sensors coupled to the plurality of RF amplifiers, each of the plurality of sensors configured to measure at least one property of a corresponding RF waveform of the plurality of RF waveforms supplied by a corresponding RF amplifier of the plurality of RF amplifiers.

In a further aspect of the present disclosure, the controller is further coupled to the plurality of sensors and is further configured to control the plurality of RF amplifiers based on the at least one property of the corresponding RF waveform.

In another aspect of the present disclosure, the plurality of RF waveforms are square waveforms.

In yet another aspect of the present disclosure, the controller is further configured to adjust the DC energy supplied by the power supply to the plurality of RF amplifiers based on at least one property of at least one RF waveform of the plurality of RF waveforms.

In another aspect of the present disclosure, at least one of the plurality of RF amplifiers is a non-resonant RF amplifier.

In an aspect of the present disclosure, a method for interdigitating waveforms for a dual-output electrosurgical generator comprises outputting DC energy from a power supply, converting DC energy from the power supply, by a plurality of amplifiers coupled to the power supply, into a plurality of RF waveforms, and controlling the plurality of RF amplifiers to interdigitate the first and second RF waveforms.

In another aspect of the present disclosure, the method further comprises measuring at a plurality of sensors coupled to the plurality of RF amplifiers at least one property of a corresponding RF waveform of the plurality of RF waveforms supplied by a corresponding RF amplifier of the plurality of RF amplifiers.

In a further aspect of the present disclosure, the method further comprises controlling the at least one of the plurality of RF amplifiers based on the at least one property of an RF waveform generated by the at least one of the plurality of RF amplifiers.

In another aspect of the present disclosure, the plurality of RF waveforms are square waveforms.

In yet another aspect of the present disclosure, the method further comprises adjusting the DC energy supplied by the power supply to the plurality of RF amplifiers based on at least one property of at least one RF waveform of the plurality of RF waveforms.

In another aspect of the present disclosure, at least one of the plurality of RF amplifiers is a non-resonant RF amplifier.

Any of the above aspects and embodiments of the present disclosure may be combined without departing from the scope of the present disclosure.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

According to embodiments of the present disclosure, an electrosurgical generator including at least a power supply and a plurality of amplifiers may be configured to power multiple instruments simultaneously. As described in more detail below, by interdigitating the waveforms corresponding to the energy output by each of the plurality of amplifiers, a peak power output, and thus the load on the power supply in, may be reduced.

A generator according to the present disclosure is configured to output electrosurgical energy suitable for performing monopolar and/or bipolar electrosurgical procedures, including, but not limited to, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing).

Figure 1:
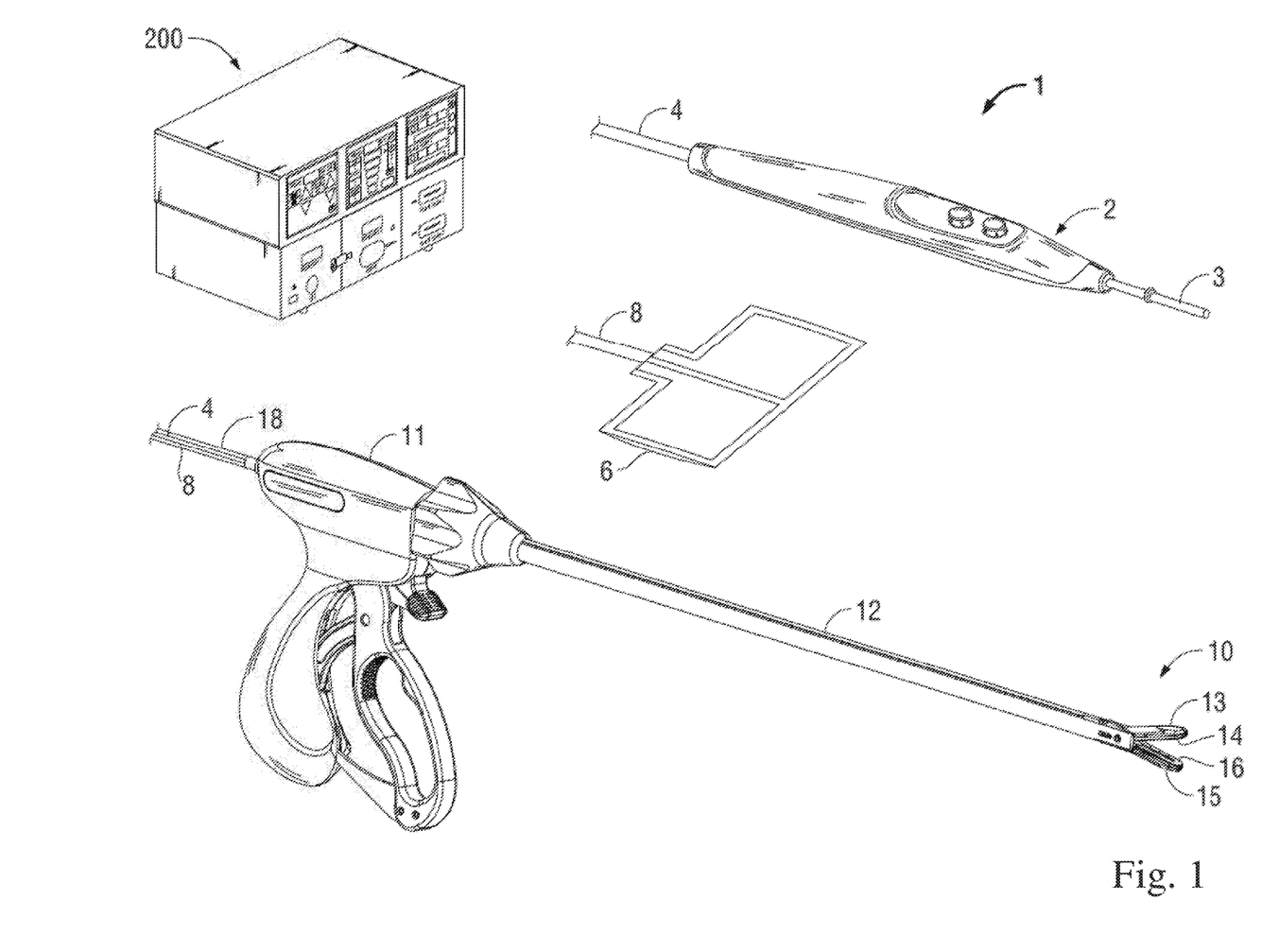
FIG. 1 is a perspective view of an electrosurgical system according to an embodiment of the present disclosure.

FIG. 1 is a schematic illustration of a bipolar and monopolar electrosurgical system 1 according to the present disclosure. System 1 may include one or more monopolar electrosurgical instruments 2 having one or more active electrodes 3 (e.g., electrosurgical cutting probe, ablation electrode(s), etc.) for treating tissue of a patient. Electrosurgical alternating current is supplied to instrument 2 by a generator 200 via a supply line 4 that is connected to an active terminal 230a, 230b (FIG. 3) of generator 200, allowing instrument 2 to cut, coagulate, ablate and/or otherwise treat tissue. The alternating current is returned to generator 200 through a return electrode 6 via a return line 8 at a return terminal 232a, 232b (FIG. 3) of generator 200. For monopolar operation, system 1 may include a plurality of return electrode pads 6 that, in use, are disposed on a patient to minimize the chances of tissue damage by maximizing the overall contact area with the patient. In addition, generator 200 and return electrode pads 6 may be configured for monitoring so-called "tissue-to-patient" contact to ensure that sufficient contact exists therebetween to further minimize chances of tissue damage.

Figure 3:
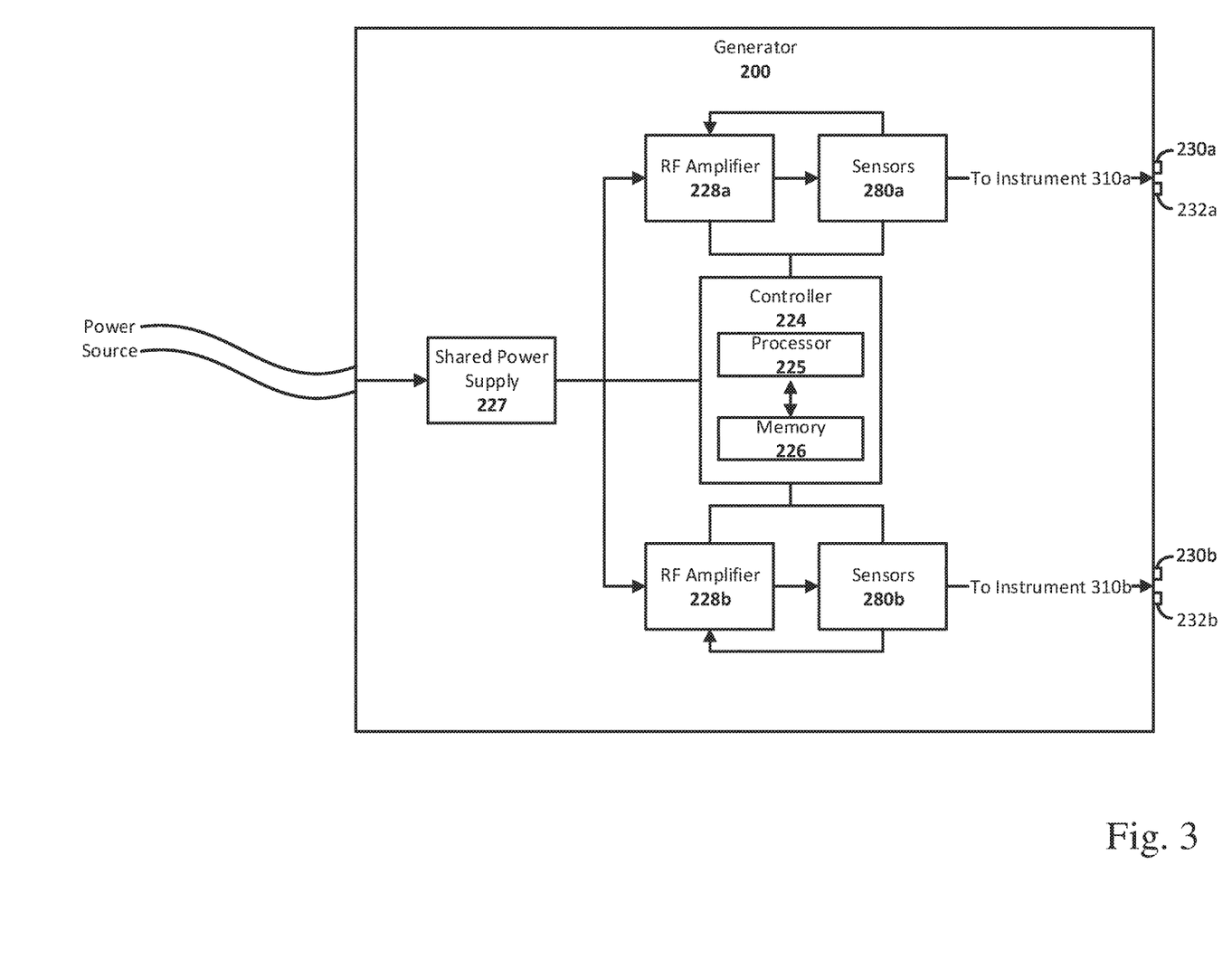
FIG. 3 is a schematic, block diagram of the electrosurgical generator of FIG. 12 according to an embodiment of the present disclosure.

System 1 may also include one or more bipolar electrosurgical instruments, for example, a bipolar electrosurgical forceps 10 having one or more electrodes for treating tissue of a patient. Electrosurgical forceps 10 includes a housing 11 and opposing jaw members 13 and 15 disposed at a distal end of a shaft 12. Jaw members 13 and 15 have one or more active electrodes 14 and a return electrode 16 disposed therein, respectively. Active electrode 14 and return electrode 16 are connected to generator 200 through a cable 18 that includes supply and return lines 4, 8 coupled to active and return terminals 230a, 230b, and 232a, 232b, respectively (FIG. 3). Electrosurgical forceps 10 is coupled to generator 200 at a connector having connections to active and return terminals 230 and 232 (e.g., pins) via a plug disposed at the end of cable 18, wherein the plug includes contacts from supply and return lines 4, 8 as described in more detail below.

Figure 2:
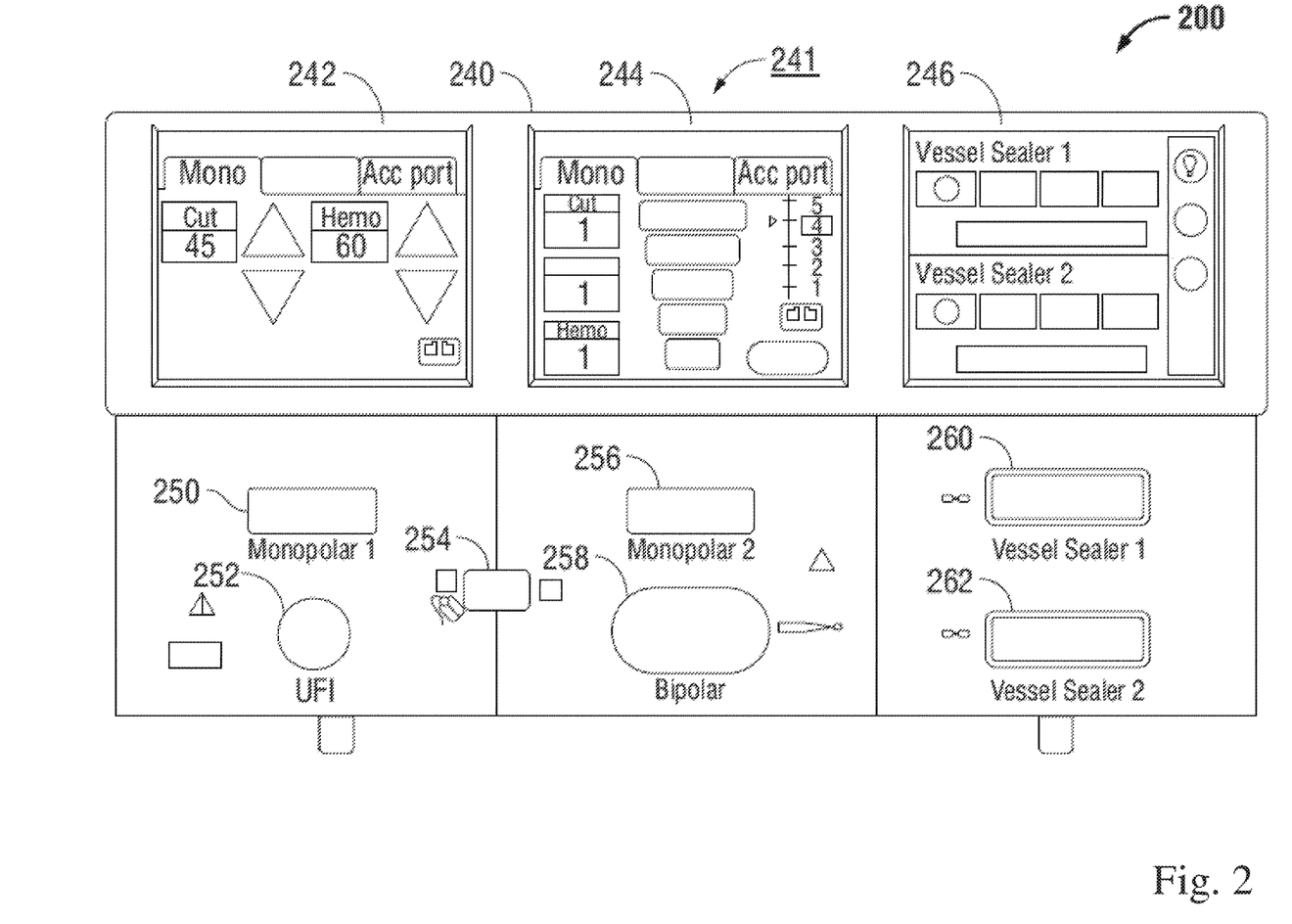
FIG. 2 is a front view of the electrosurgical generator of FIG. 1 according to an embodiment of the present disclosure.

With reference to FIG. 2, a front face 240 of generator 200 is shown. Generator 200 may be any suitable type (e.g., electrosurgical, microwave, etc.) and may include a plurality of connectors 250-262 to accommodate various types of electrosurgical instruments (e.g., electrosurgical forceps 10, etc.).

Generator 200 includes a user interface 241 having one or more display screens or information panels 242, 244, 246 for providing the user with variety of output information (e.g., intensity settings, treatment complete indicators, etc.). Each of screens 242, 244, 246 is associated with a corresponding connector 250-262. Generator 200 includes suitable input controls (e.g., buttons, activators, switches, touch screen, etc.) for controlling generator 200. Display screens 242, 244, 246 are also configured as touch screens that display a corresponding menu for the electrosurgical instruments (e.g., electrosurgical forceps 10, etc.). The user then adjusts inputs by simply touching corresponding menu options.

Screen 242 controls monopolar output and the devices connected to connectors 250 and 252. Connector 250 is configured to couple to a monopolar electrosurgical instrument (e.g., electrosurgical instrument 2) and connector 252 is configured to couple to a foot switch (not shown). The foot switch provides for additional inputs (e.g., replicating inputs of generator 200). Screen 244 controls monopolar and bipolar output and the devices connected to connectors 256 and 258. Connector 256 is configured to couple to other monopolar instruments. Connector 258 is configured to couple to a bipolar instrument (not shown).

Screen 246 controls bipolar sealing procedures performed by forceps 10 that may be plugged into connectors 260 and 262. Generator 200 outputs energy through connectors 260 and 262 suitable for sealing tissue grasped by forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to controller 224 where the setting may be saved in memory 226. In embodiments, the intensity setting may be a number scale, for example, from one to ten or one to five. In embodiments, the intensity setting may be associated with an output curve of generator 200. The intensity settings may be specific for each forceps 10 being utilized, such that various instruments provide the user with a specific intensity scale corresponding to forceps 10.

Generator 200 according to the present disclosure is a non-resonant generator and may include dual or multiple outputs to simultaneously power multiple instruments.

The generator 200 may be configured to operate in any of a constant voltage limit mode, a constant current limit mode, a constant power mode, and combinations thereof. The mode selection is generally based on the impedance associated with the tissue being cut. Different types of tissue, such as muscle and fat, have different impedances. In terms of electrosurgical operations, constant power output tends to uniformly vaporize tissue, resulting in clean dissection. Whereas constant voltage output tends to explosively vaporize or carbonize tissue ("black coagulation"), and constant current output tends to thermally coagulate tissue without vaporization ("white coagulation"). Carbonization is surgically useful if the surgeon wishes to rapidly destroy surface tissue, and thermal coagulation is regularly coupled with mechanical pressure to seal hepatic or lymphatic vessels shut. However, the surgeon generally desires to operate using constant power output and importantly, return to using constant power output as quickly as possible if there is deviation.

Figure 5:
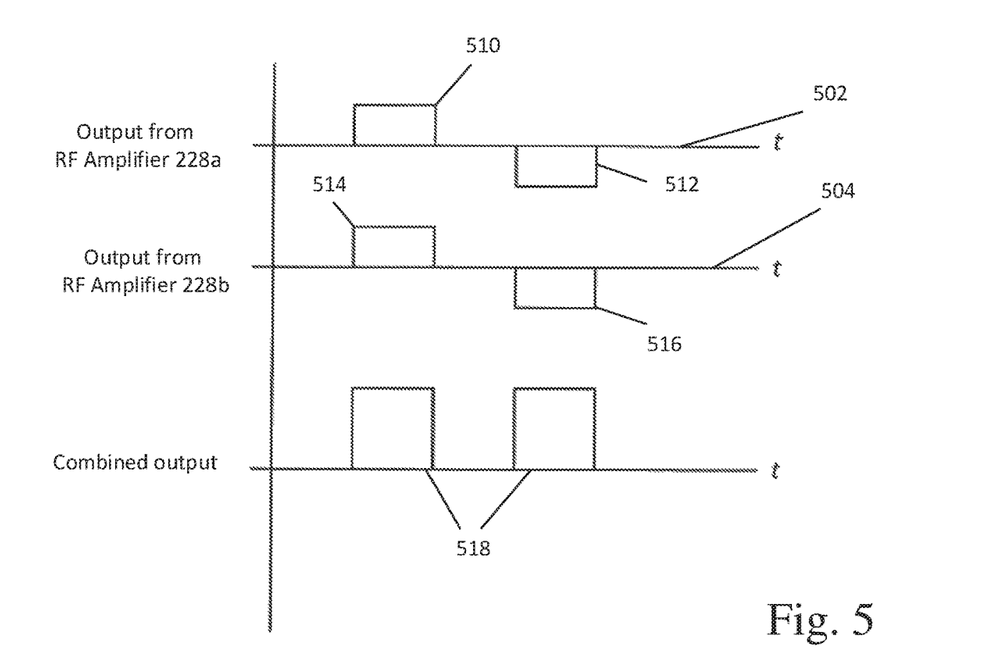
FIG. 5 is a graphical representation of power output levels of the electrosurgical generator of FIG. 1 having multiple outputs according to an embodiment of the present disclosure.

With respect to the AC output of the generator 200 and in exemplary embodiments, "constant power" is defined to mean the average power delivered in each switching cycle is substantially constant. Likewise, "constant voltage" and "constant current" are defined as modes where the root mean square (RMS) value of the AC voltage or current, respectively, is regulated to a substantially fixed value. An exemplary graphical representation of the desired output characteristics is illustrated in FIG. 5. In an exemplary embodiment, as the load impedance increases and voltage increases, the corresponding increasing output voltage triggers a transition from a constant current mode shown as region A to a constant power mode shown as region B and to a constant voltage mode shown as region C. Similarly, in an exemplary embodiment, as the load impedance decreases and current increases, the corresponding decreasing output voltage triggers the opposite transition from the constant voltage region C to the constant power region B and to the constant current region A.

FIG. 3 shows a schematic block diagram of generator 200 configured to output electrosurgical energy. Generator 200 includes a controller 224, a power supply 227, radiofrequency (RF) amplifiers 228a, 228b, and sensors 280a, 280b. Power supply 227 may be a high voltage, DC power supply connected to an AC source (e.g., line voltage) and provides high voltage, DC power to RF amplifiers 228a, 228b, which then converts high voltage, DC power into treatment energy (e.g., electrosurgical or microwave) and delivers the energy to active terminals 230a, 230b, respectively. The energy is returned thereto via return terminals 232a, 232b. RF amplifiers 228a, 228b are configured to operate in a plurality of modes, during which generator 200 outputs corresponding waveforms having specific duty cycles, peak voltages, crest factors, etc. It is envisioned that in other embodiments, generator 200 may be based on other types of suitable power supply topologies. RF amplifiers 228a, 228b may be non-resonant RF amplifiers. A non-resonant RF amplifier, as used herein, denotes an amplifier lacking any tuning components, i.e., conductors, capacitors, etc., disposed between the RF inverter and the load.

Controller 224 includes a processor 225 operably connected to a memory 226, which may include transitory type memory (e.g., RAM) and/or non-transitory type memory (e.g., flash media, disk media, etc.). Processor 225 includes an output port that is operably connected to power supply 227 and/or RF amplifiers 228a, 228b allowing processor 225 to control the output of generator 200 according to either open and/or closed control loop schemes. A closed loop control scheme is a feedback control loop, in which a plurality of sensors 280a, 280b measure a variety of tissue and energy properties (e.g., tissue impedance, tissue temperature, output power, current and/or voltage, etc.), and provide feedback to controller 224. Controller 224 then signals power supply 227 and/or RF amplifiers 228a, 228b, which adjusts the DC and/or power supply, respectively. Those skilled in the art will appreciate that processor 225 may be substituted for by using any logic processor (e.g., control circuit) adapted to perform the calculations and/or set of instructions described herein including, but not limited to, field programmable gate array, digital signal processor, and combinations thereof.

Generator 200 according to the present disclosure includes a plurality of sensors 280a, 280b, i.e., RF current sensors and RF voltage sensors. Various components of generator 200, namely, RF amplifiers 228a, 228b, and sensors 280a, 280b, may be disposed on a printed circuit board (PCB). An RF current sensor may be coupled to active terminals 230a, 230b and provide measurements of the RF current supplied by RF amplifiers 228a, 228b. An RF voltage sensor may be coupled to active terminals 230a, 230b and return terminals 232a, 232b provides measurements of the RF voltage supplied by RF amplifiers 228a, 228b.

Sensors 280a, 280b provide the sensed RF voltage and current signals, respectively, to controller 224, which then may adjust output of power supply 227 and/or RF amplifiers 228a, 228b in response to the sensed RF voltage and current signals. Controller 224 also receives input signals from the input controls of generator 200, instrument 2 and/or forceps 10. Controller 224 utilizes the input signals to adjust power outputted by generator 200 and/or performs other control functions thereon.

Figure 4:
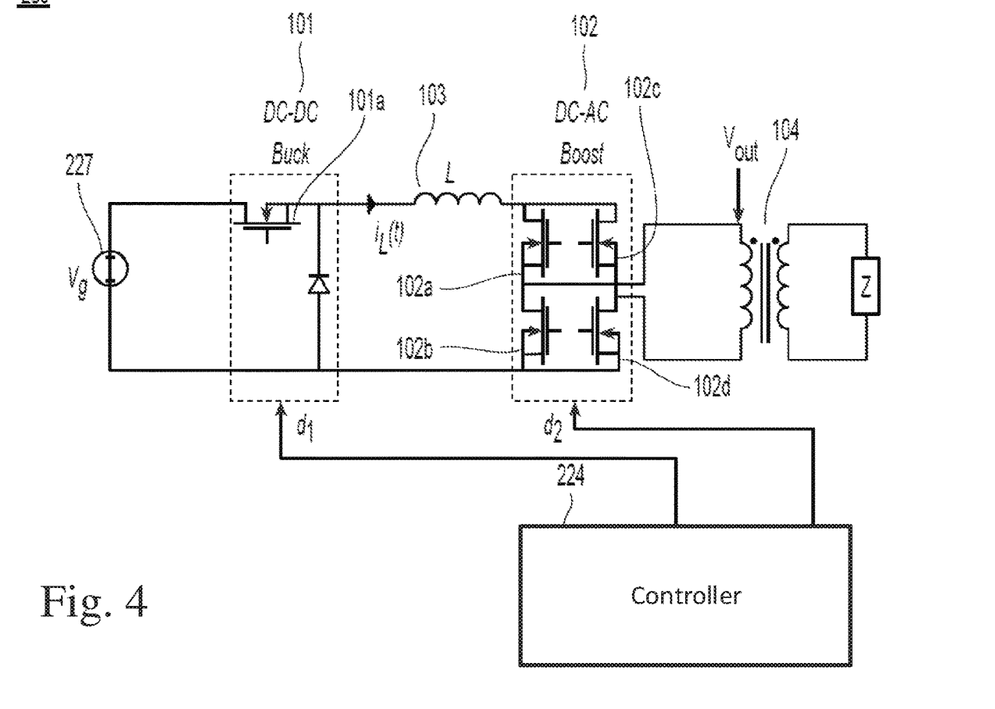
FIG. 4 is a schematic, block diagram of a DC-DC converter and a DC-AC inverter of the electrosurgical generator of FIG. 1 according to an embodiment of the present disclosure.

With reference to the schematic shown in FIG. 4, the generator 200 includes a DC-DC buck converter 101, a DC-AC boost converter 102, an inductor 103, a transformer 104, and controller 224. In embodiments, the DC-AC boost converter 102 is part of each of the RF amplifiers 228a, 228b. Accordingly, for simplicity only one of the RF amplifiers 228a, 228b is discussed herein below. In the exemplary embodiment, a DC voltage source Vg, such as power supply 227, is connected to DC-DC buck converter 101. Furthermore, inductor 103 is electrically coupled between DC-DC buck converter 101 and DC-AC boost converter 102. The output of DC-AC boost converter 102 transmits power to the primary winding of transformer 104, which passes through the secondary winding of transformer 104 to the load Z (e.g., tissue being treated).

DC-DC buck converter 101 includes a switching element 101a and DC-AC boost converter 102 includes a plurality of switching elements 102a-102d arranged in an H-bridge topology. In embodiments, DC-AC boost converter 102 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In an exemplary embodiment, controller 224 is in communication with both DC-DC buck converter 101 and DC-AC boost converter 102, in particular, the switching elements 101a and 102a-102d, respectively. Controller 224 is configured to output control signals, which may be a pulse-width modulated signal, to switching elements 101a and 102a-102d as described in further detail in co-pending application published as US 2014/0254221, entitled CONSTANT POWER INVERTER WITH CREST FACTOR CONTROL, filed on Dec. 4, 2013 by Johnson et al., the entire contents of which is incorporated by reference herein. In particular, controller 224 is configured to control the duty cycle d1 of the control signal supplied to switching element 101a of DC-DC buck converter 101 and duty cycle d2 of the control signals supplied to switching elements 102a-102d of DC-AC boost converter 102. Additionally, controller 224 is configured to measure power characteristics of generator 200, and control generator 200 based at least in part on the measured power characteristics. Examples of the measured power characteristics include the current through inductor 103 and the voltage at the output of DC-AC boost converter 102. In an exemplary embodiment, controller 224 controls buck converter 101 by generating the duty cycle d1 based on a comparison of the inductor current and a nonlinear carrier control current for every cycle.

FIG. 5 is a plot showing the power output levels of the generator 200. In response to one of the instruments 310a or 310b being activated, a corresponding RF amplifier 228a or 228b generates the programmed treatment energy for the instrument. To generate treatment energy, RF amplifiers 228a, 228b draw DC power from shared power supply 227.

In response to both instruments 310a and 310b being activated simultaneously, each of the RF amplifiers 228a and 228b generates energy for each of the instruments 310a and 310b. The non-resonant RF amplifiers 228a and 228b according to the present disclosure are configured to generate square waveforms as shown in FIG. 5, rather than sine waveforms, which are generated by resonant networks that are absent from the RF amplifiers 228a and 228b. With continued reference to FIG. 5, output generated by RF amplifier 228a is represented by a first waveform 502 having peaks 510 and 512, and output generated by RF amplifier 228b is represented by a second waveform 504 having peaks 514 and 516. The combined output of RF amplifiers 228a, 228b is represented by peaks 518, each of which is a combination of peaks 510 and 514 and peaks 512 and 516.

Thus, when instruments 310a, 310b are activated simultaneously, with treatment energy being delivered in-phase, the total peak power sourced by shared power supply 227 is the sum of individual outputs, requiring shared power supply 227 to be rated for this higher peak power. To avoid this, the power levels drawn from shared power supply 227 may be interspersed such that peak power levels are not drawn by multiple RF amplifiers 228a and 228b simultaneously. One method of interspersing power drawing levels is by interdigitating the waveforms. Interdigitation, as used herein, denotes outputting two or more waveforms at a specific phase relationship in which the power draw from the power supply 227 is substantially uniform. In one embodiment, waveforms may be interdigitated such that their respective peaks are evenly spaced and occur out of phase. The peaks of one waveform may be aligned with the valleys of the other waveform. By doing so, the power levels drawn balance out, and results in a constant level of power drawn instead of peaks and valleys.

Figure 6:
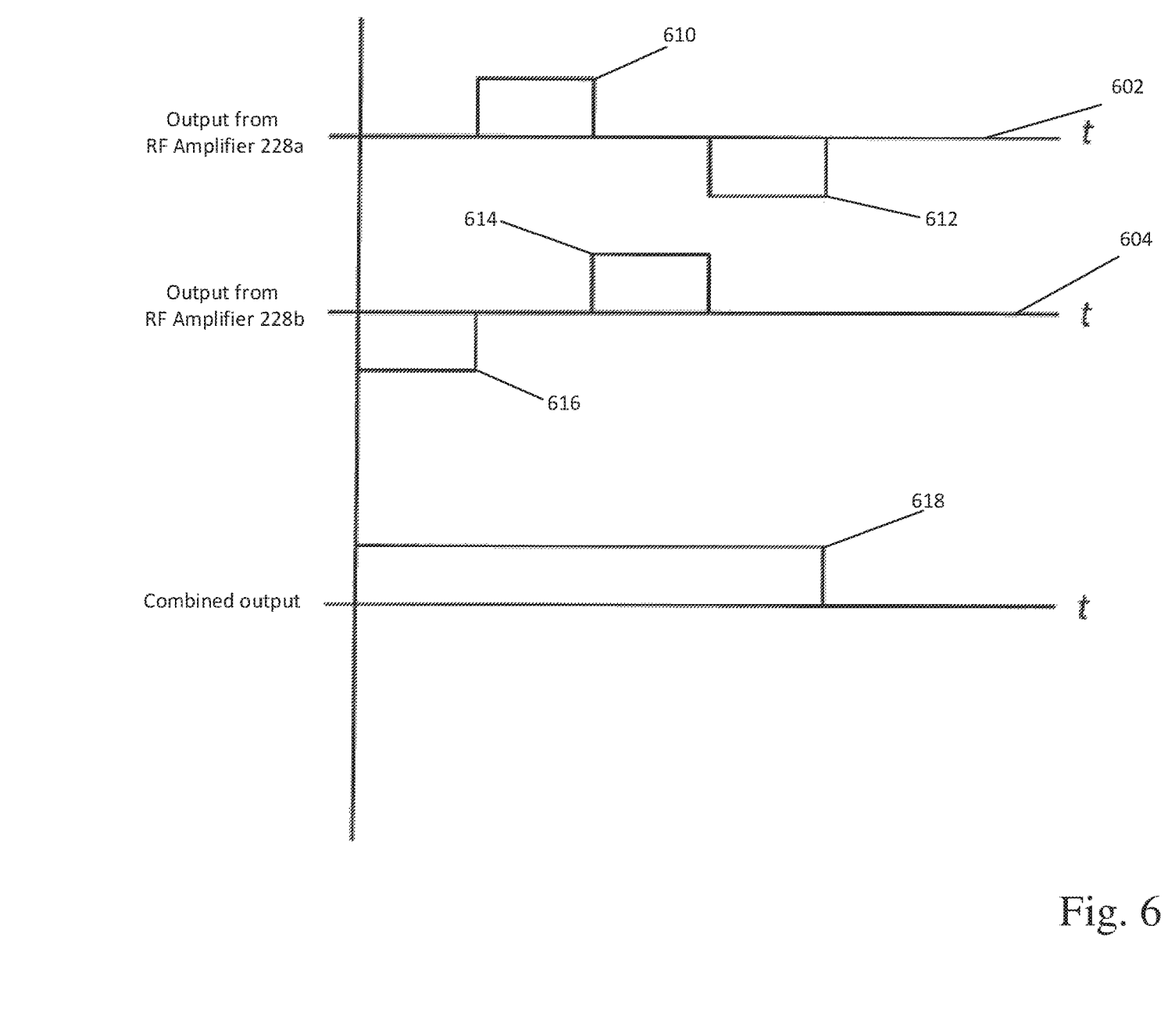
FIG. 6 is another graphical representation of power output levels of the electrosurgical generator of FIG. 1 having multiple outputs according to an embodiment of the present disclosure.

FIG. 6 is a plot showing the power output levels of generator 200 when the waveforms generated by RF amplifiers 228a, 228b are interdigitated. Output of the RF amplifier 228a is represented by a first waveform 602 having peaks 610, 612 and output of the RF amplifier 228b is represented by a second waveform 604 having peaks 614 and 616. The combined output of RF amplifiers 228a, 228b when the respective output waveforms 602 and 604 are interdigitated may be represented by a single, continuous waveform 618, without any peaks, because the power output level remains constant. Thus, when dual output waveforms are interdigitated, as shown in FIG. 6, the peak power delivered by shared power supply 227 may be reduced as compared to the output illustrated in FIG. 5.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An electrosurgical generator, comprising:
   a plurality of RF amplifiers, each of the plurality of RF amplifiers configured to output an RF waveform of a plurality of RF waveforms;

a plurality of pairs of output terminals, each pair including an active terminal and a return terminal, each of the pairs of output terminals is independently connected to one of the plurality of RF amplifiers and configured to independently connect to an electrosurgical instrument of a plurality of electrosurgical instruments; and a controller coupled to the plurality of RF amplifiers and configured to control the plurality of RF amplifiers to interdigitate the plurality of RF waveforms.

2. The electrosurgical generator according to claim 1, further comprising a plurality of sensors coupled to the plurality of RF amplifiers, each of the plurality of sensors configured to measure at least one property of a corresponding RF waveform of the plurality of RF waveforms supplied by a corresponding RF amplifier of the plurality of RF amplifiers.

3. The electrosurgical generator according to claim 2, wherein the controller is further coupled to the plurality of sensors and is further configured to control the plurality of RF amplifiers based on the at least one property of the corresponding RF waveform.

4. The electrosurgical generator according to claim 1, further comprising a power supply coupled to each amplifier of the plurality of RF amplifiers and configured to output DC energy, wherein each amplifier of the plurality of RF amplifiers is configured to convert the DC energy into the RF waveforms.

5. The electrosurgical generator according to claim 4, wherein the controller is further configured to adjust the DC energy supplied by the power supply to the plurality of RF amplifiers based on at least one property of at least one RF waveform of the plurality of RF waveforms.

6. The electrosurgical generator according to claim 1, wherein at least one of the plurality of RF amplifiers is a non-resonant RF amplifier.

7. The electrosurgical generator according to claim 5, wherein interdigitation of the plurality of RF waveforms includes outputting each of the plurality of RF waveforms out of phase with other waveform of the plurality of RF waveforms.

8. A system for interdigitating waveforms for a dual-output electrosurgical generator, the system comprising:
an electrosurgical generator including:

a plurality of RF amplifiers, each of the plurality of RF amplifiers configured to output an RF waveform of a plurality of RF waveforms;

a plurality of pairs of output terminals, each pair including an active terminal and a return terminal, each of the pairs of output terminals is independently connected to one of the plurality of RF amplifiers; and a controller coupled to the plurality of RF amplifiers and configured to control the plurality of RF amplifiers to interdigitate the plurality of RF waveforms; and a plurality of electrosurgical instruments, each of which is operatively coupled to one of the plurality of pairs of output terminals of the dual-output electrosurgical generator, wherein each of the electrosurgical instruments is coupled to one of the plurality of RF amplifiers.

9. The system according to claim 8, wherein the electrosurgical generator further includes a plurality of sensors coupled to the plurality of RF amplifiers, each of the plurality of sensors configured to measure at least one property of a corresponding RF waveform of the plurality of RF waveforms supplied by a corresponding RF amplifier of the plurality of RF amplifiers.

10. The system according to claim 9, wherein the controller is further coupled to the plurality of sensors and is further configured to control the plurality of RF amplifiers based on the at least one property of the corresponding RF waveform.

11. The system according to claim 8, wherein the electrosurgical generator further includes a power supply coupled to each of the plurality of RF amplifiers and configured to output DC energy, wherein each of the plurality of RF amplifiers is configured to convert the DC energy into the RF waveforms.

12. The system according to claim 11, wherein the controller is further configured to adjust the DC energy supplied by the power supply to the plurality of RF amplifiers based on at least one property of at least one RF waveform of the plurality of RF waveforms.

13. The system according to claim 12, wherein at least one of the plurality of RF amplifiers is a non-resonant RF amplifier.

* * * * *